United States Patent [19]

Rubinstein et al.

[11] Patent Number: 5,007,834
[45] Date of Patent: Apr. 16, 1991

[54] MANUFACTURE AND INSTALLATION OF A DENTAL PROSTHESIS

[76] Inventors: Sergio Rubinstein, 1451 Brandywine La., Buffalo Grove, Ill. 60089; Masayuki Hoshi, 9004 Kennedy Dr., Des Plaines, Ill. 60016

[21] Appl. No.: 420,274

[22] Filed: Oct. 12, 1989

[51] Int. Cl.$^5$ .................................................. A61C 8/00
[52] U.S. Cl. ..................................... 433/173; 433/213
[58] Field of Search ............... 433/173, 174, 176, 213, 433/220, 221, 223

[56] References Cited

U.S. PATENT DOCUMENTS

| | | | |
|---|---|---|---|
| 1,583,459 | 5/1926 | Hansen | 433/220 |
| 3,925,892 | 12/1975 | Juillet | 433/176 |
| 4,355,978 | 10/1982 | Ericson | 433/220 |
| 4,531,915 | 7/1985 | Tatum, Jr. | 433/176 |
| 4,744,756 | 5/1988 | Ross | 433/173 |

OTHER PUBLICATIONS

The International Journal of Periodontics & Restorative Dentistry, Jun. 1988, pp. 25–32.
Implant Innovations Incorporated Catalog, including list effective 3/89, p. 2.
Restorative References Guide, 3/87, cover page.

Primary Examiner—John J. Wilson
Attorney, Agent, or Firm—Willian, Brinks, Olds, Hofer, Gilson & Lione

[57] ABSTRACT

Articles used in the manufacture of a dental prosthesis, including components thereof, are disclosed. In one aspect of the invention, such articles, include a meltable, threaded shank which can be screwed into an analog of a surgically placed implant member for fabricating support structure for the prosthesis.

17 Claims, 3 Drawing Sheets

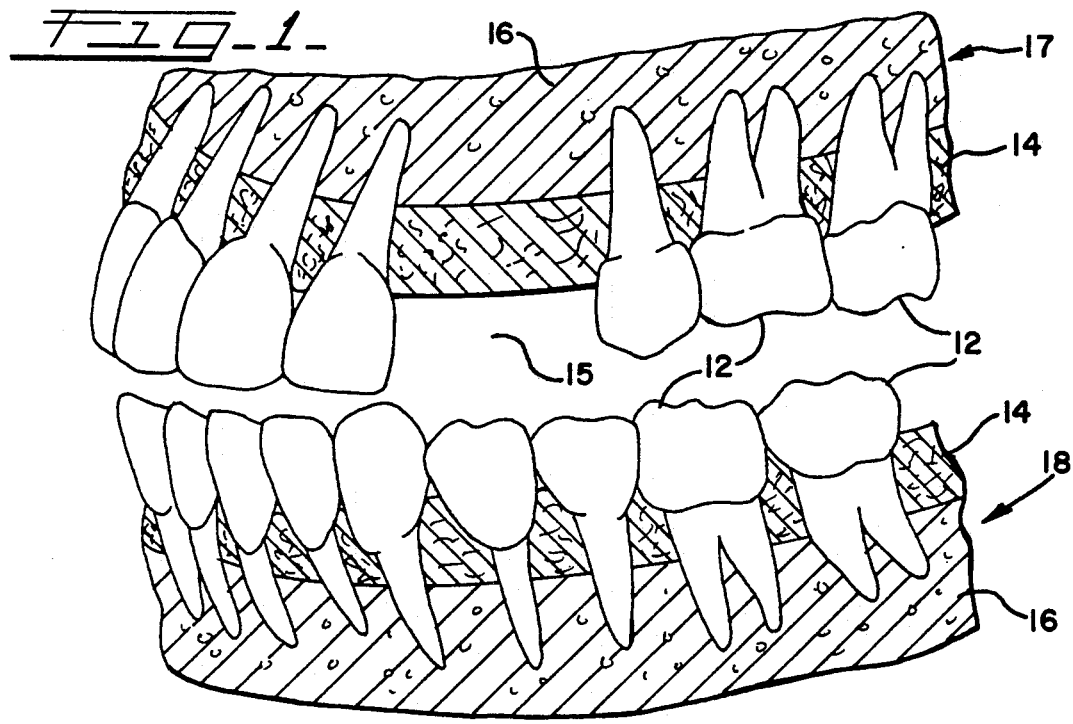

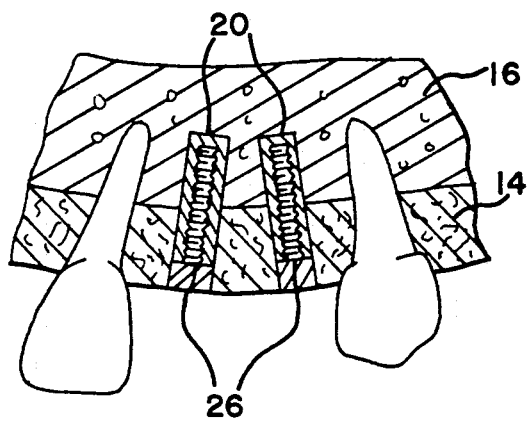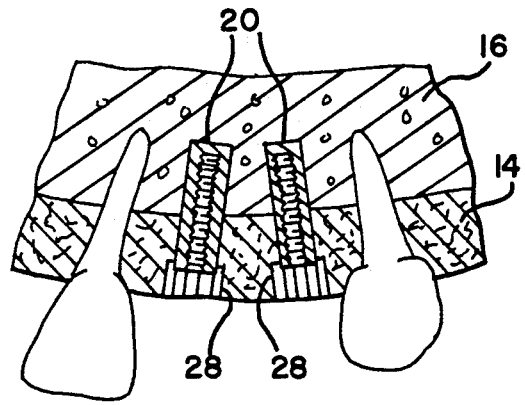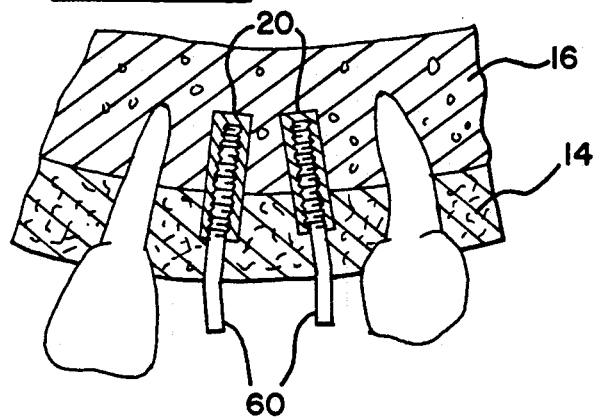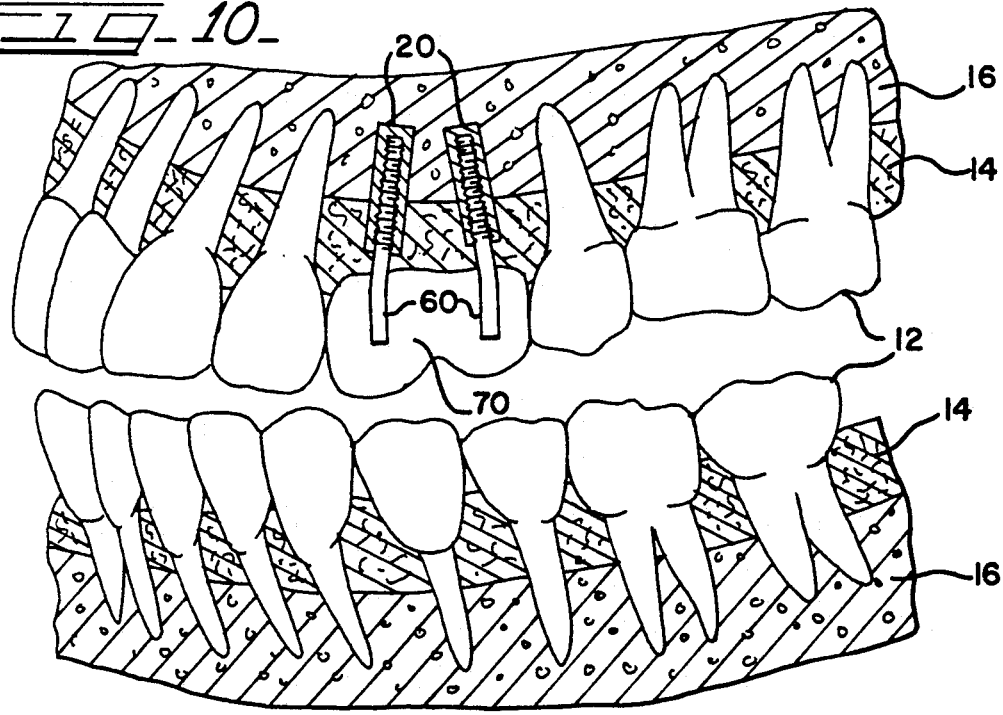

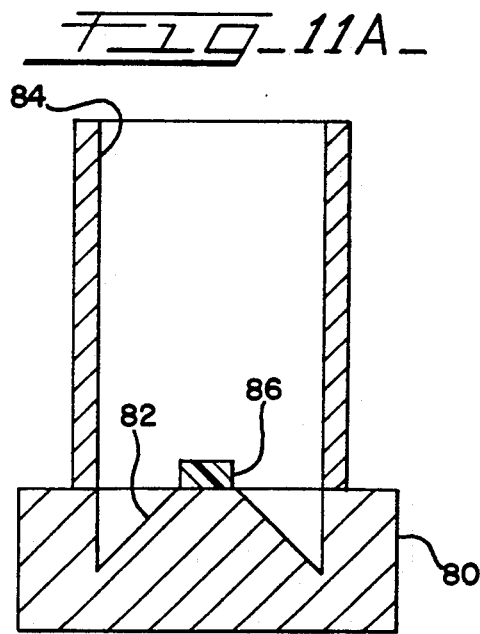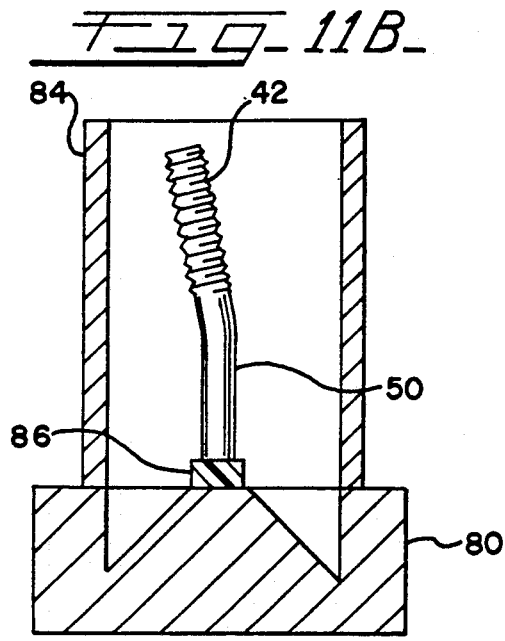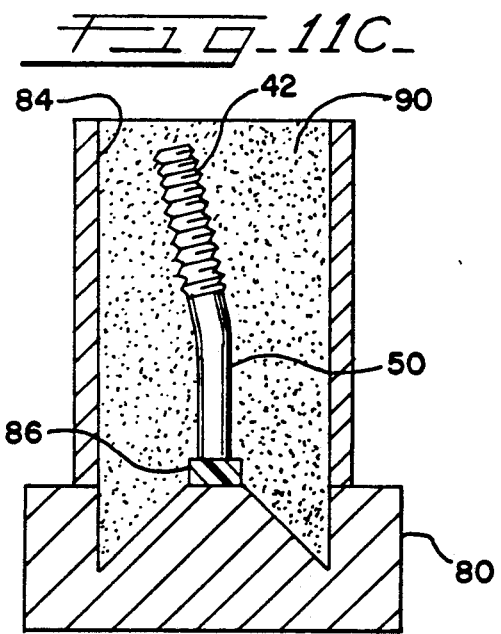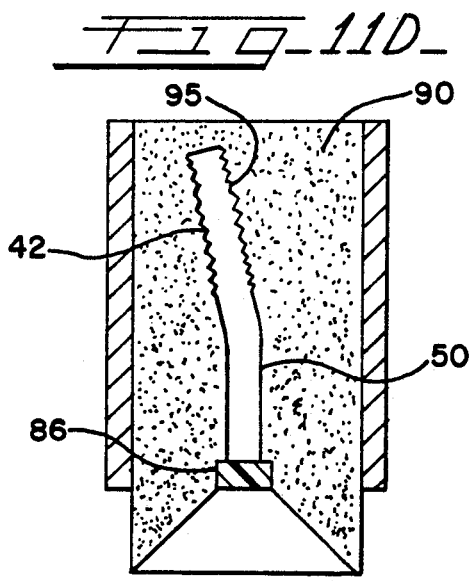

MANUFACTURE AND INSTALLATION OF A DENTAL PROSTHESIS

BACKGROUND OF THE INVENTION

This invention generally relates to a dental prosthesis, and in particular to improvements in articles used in the manufacture of a dental prosthesis, components thereof, and methods for manufacturing such articles and components.

More particularly this invention relates to a dental prosthesis of the type utilizing an implant member, having a threaded bore, which is adapted to be surgically placed beneath gum tissue and into underlying bone structure. Conventionally, there is provided a straight prosthesis support having a threaded portion at its lower end and a post at its upper end. The threaded portion of the straight prosthesis support is sized so that it can be threaded into the surgically placed implant member. The post thus extends into the mouth and serves as a supporting structure for a dental prosthesis such as a crown or bridge.

Unfortunately, straight prosthesis support structures of the type described suffer from certain drawbacks and deficiencies. For example, if the implant member, when surgically placed, is not precisely oriented relative to the mouth and gums, the post at the upper end of the support structure will extend crookedly into the mouth when the threaded portion is screwed into the implant member. This, in turn, typically results in a poorly-fitting, misaligned, or otherwise esthetically or functionally deficient prosthesis. Often such a prosthesis must be replaced or refitted, resulting in considerable discomfort, inconvenience and expense for the patient.

Moreover, even when the implant member is precisely oriented, so that the post extends straight into the mouth when the threaded portion of the support structure is screwed into the implant member, a poorly-fitting or misaligned prosthesis may result. This is due to the fact that often times a proper-fitting prosthesis requires that the post extend into the mouth at a specific angle, depending on the geometry of the patient's mouth and teeth.

In an effort to overcome problems of the type described, there has been developed support structure comprising a base member and separate post member. The base member typically has a lower threaded section, an intermediate flange section and an upper extension section. The intermediate flange section may be characterized by a hexagonal seat for orienting the separate post member in any one of several directions.

The separate post member typically has a lower angled section and an upper prosthesis supporting section. The lower angled section conventionally defines a bore which extends obliquely from the bottom surface through a side surface of the angled section. The opening in the bottom surface may be twelve-pointed, and sized to fit over the hexagonal seat in the flange portion of the base member in any one of multiple positions.

In application, the threaded section of the base member is screwed into the implant member with the upper extension section extending into the mouth. The opening in the bottom surface of the angled section is then fitted over the upper extension section and seated onto the hexagonal seat in the flange section of the base member. The orientation of the angled section, and hence the orientation of the upper supporting section, can thus be adjusted to any one of the numerous positions defined by the twelve-pointed opening. This gives the dental professional many alternatives in trying to fabricate a dental prosthesis that will fit properly in the mouth. Moreover, by making several different angled sections, each such section having a bore that extends at a different oblique angle through the bottom surface, the dental professional is afforded substantial flexibility in installing a supporting structure for a dental prosthesis which extends into the mouth at the proper orientation in an effort to provide a proper fit.

Though the system described above, utilizing a base member and separate post member, has been successfully used, it too is not without certain inherent deficiencies. First, even though the twelve-pointed opening, along with the variety of available angled sections, afford substantial flexibility in fabricating a supporting structure for a dental prosthesis, the angles and orientations so afforded are nonetheless limited. Moreover, after the angled section of the post member has been fitted over the extension section of the base member, the extension member typically extends so far through the side surface of the angled section that its end must be severed by the dental professional. Thus, this system entails substantial additional effort on the part of the dental professional, and still does not ensure a custom fit in view of the finite angles and orientations that can be achieved.

It is thus a primary object of this invention to provide improved articles utilized in manufacturing a dental prosthesis, along with improved components therefor. It is also an object of this invention to provide an improved method for manufacturing such articles and components. It is a further object of this invention to provide such articles and components which permit a wider variety of angles and positions for a support member for a dental prosthesis than have ordinarily been available heretofore.

SUMMARY OF THE INVENTION

The objects of the invention enumerated above, along with numerous advantages and features, are achieved in an article used in the manufacture of a dental prosthesis of the type utilizing an implant member, having a threaded bore, adapted to be surgically placed beneath gum tissue and into underlying bone structure. The article comprises a meltable shank, means defining threads on the shank of a gauge which would be cooperative with the threaded bore of the implant member, and means defining an upper surface of the shank adapted to have formed thereon a meltable model of a post for the prosthesis.

The meltable shank and the meltable model of the post can be covered with a dental investment, and then melted away to leave a mold therein. The mold can then be used to form a one-piece prosthesis support that can be screwed into the implant member. Since the meltable model of the post can be formed of wax, or some other suitable material, and made to almost precisely correspond to the geometry of the post needed for a particular patient, the resulting one-piece prosthesis support will meet the needs of the particular patient for whom it was made.

In another aspect of the invention there is provided a one-piece support member used in the manufacture of a dental prosthesis of the type utilizing an implant member as previously described. The one-piece support member includes a shank portion having threads of a gauge which would permit screw-in insertion into the bore of the implant member, and a post portion having a proximal portion integrally formed with the shank portion. The post portion further includes a distal portion extending at an obtuse angle relative to the shank.

The one-piece member of the type described is preferably made from a mold formed in a dental investment as explained above. Since the meltable model used in making that mold is formed by the dental professional to precisely fit the geometry of a particular patient's mouth, the resulting one-piece support member, including the post portion, extends into the patient's mouth the proper distance and at the proper angle to optimize the fabrication and affixation of the dental prosthesis for that patient.

In another aspect of the invention, there is provided a method for making an article used in the manufacture of a dental prosthesis, and components therefor, of the type utilizing an implant member as previously described. The method includes the steps of providing an analog of the implant member, providing a temporary threaded shank formed of meltable material, screwing the shank into the analog, and forming on the upper surface of the shank a meltable model of a post for the prosthesis, the model also being formed of meltable material.

Using the method so described, a dental investment may be formed around the model and at least a portion of the shank. The model and then the shank may be melted away to form a mold within the investment for a prosthesis support that can be screwed into the bore of an implant member The mold may then be filled with molten material, such as a metal, which can then be allowed to harden into a one-piece support member. The one-piece support member may then be removed from the investment and screwed into the implant member. In applications where two such implant members, and two such one-piece members are utilized, a dental prosthesis, such as a bridge, can then be formed over the two support members.

DESCRIPTION OF THE DRAWINGS

Exemplary embodiments of the invention summarized above are illustrated in the accompanying drawings wherein:

FIG. 1 is a schematic drawing of a patient's mouth illustrating an application where a dental prosthesis, such as a bridge, may be prescribed;

FIG. 2 is a schematic drawing of an implant member which can be surgically placed beneath gum tissue and into underlying bone structure for installing such a dental prosthesis;

FIG. 3 is a schematic drawing of an analog of the implant member shown in FIG. 1, the analog being used in making components of such a prosthesis;

FIG. 4 is a schematic drawing of a shank used in making components of such a prosthesis;

FIG. 5 is a schematic drawing of a model of a post, adapted to be formed on the shank shown in FIG. 4, also used in making components of such a prosthesis;

FIG. 6 is a schematic drawing of a one-piece support member which can be screwed into the implant member shown in FIG. 2, and used for supporting such a prosthesis;

FIG. 7 is a schematic drawing of a pair of implant members of the type shown in FIG. 2 surgically placed in the mouth of the patient shown in FIG. 1;

FIG. 8 is a schematic drawing of the implant members shown in FIG. 7 with a temporary cap placed thereon;

FIG. 9 is a schematic drawing of the implant members shown in FIG. 7 with a one-piece support member of the type shown in FIG. 6 screwed into each implant member;

FIG. 10 is a schematic drawing of the implant members shown in FIG. 7 with a prosthesis installed; and FIGS. 11A-11D are schematic drawings illustrating the steps that may be used in making the one-piece support member shown in FIG. 6.

DETAILED DESCRIPTION OF EXEMPLARY EMBODIMENTS

Referring now to FIG. 1, there is shown, in schematic form, a patient's mouth represented by reference numeral 10. Mouth 10 has an upper jaw 17 and a lower jaw 18, each characterized by gum tissue 14, underlying bone structure 16 and a plurality of teeth 12. Reference numeral 15 represents a space, devoid of teeth, for which a prosthesis, such as a bridge, has been prescribed by a dental professional.

Such a prosthesis typically requires an implant member 20 of the type shown in FIG. 2. Implant member 20 conventionally comprises a substantially cylindrical shaft 22 having a threaded bore 24. Such implant members are typically made of Titanium, or any other suitable material, and are well known to those skilled in the art.

The installation of a dental prosthesis of the type which utilizes an implant member 20 that is surgically placed beneath gum tissue and into underlying bone structure conventionally involves a prolonged process by one or more dental professionals. Typically, after a diagnosis has been made, and a surgical procedure has been prescribed, the patient is anesthetized, and a small incision is made in the gum tissue at a location beneath which the implant member is to be placed. As used herein, the terms "beneath" and "underlying" refer to the direction extending the crown of a tooth toward its root, whether the tooth be located in the upper or lower jaw of a patient.

In applications where two such implant members are required, such as where a bridge is needed, two such incisions are made at locations whose distance therebetween is approximately equal to the span of the bridge. At the location of each incision, the gums are reflected and a hole is then drilled into the underlying bone structure. Preferably, the diameter of the hole is substantially equal to the diameter of the implant member, and the depth of the hole is somewhat greater than the length of the implant member. As shown in FIG. 7, the implant members are then placed in their respective holes. A Titanium screw 26 is then preferably inserted into the implant members to prevent the threaded bores thereof from becoming filled with human tissue. The incisions in the gums are then sutured.

After the implant members become integrated into the bone structure, six months for example, the patient then returns to the dental professional and is again anesthetized. A small incision is then made in the gum tissue to provide access to the implant members that have been previously placed in the mouth, and the Titanium screws 26 are removed. As shown in FIG. 8, a temporary healing cap 28, typically made of plastic, serves to keep the threaded bore of the implant member covered, without losing access to the implant member.

After a relatively short period of time, two weeks for example, the patient again returns to the dental professional, and the temporary healing caps 28 are removed from their respective implant members 20. A conventional stainless steel transfer pin (not shown) is then screwed into the threaded bore of each implant member, and an impression is taken of the patient's mouth. Such an impression is typically made using rubber base or vinyl-poly siloxane material which hardens in only a few minutes. After hardening, the impression is removed from the mouth. The transfer pins are then unscrewed from the implant members and inserted into the impression—threaded end out. After reinstalling healing caps 28, the patient may then be excused.

A conventional analog of implant member 20, represented by reference numeral 30 in FIG. 3, comprises a substantially cylindrical shaft 32 and a threaded bore 34. Analog 30 is conventionally screwed onto the threaded end of each transfer pin. The entire impression, including the analogs 30, are then covered with conventional dental stone. When the dental stone hardens, it is removed from the impression, resulting in a facsimile of the patient's mouth, including the analogs which are representative of the surgically placed implant members.

The preceding description summarizes what is understood to be a conventional procedure typically performed by a dental professional. One exemplary description of this type of surgical procedure is described at pages 28–32 of the June, 1988 issue of "The International Journal of Periodontics and Restorative Dentistry," which is incorporated herein by reference. Such a procedure may further include the selection of a straight prosthesis support structure of the prior art, and/or appropriately angled two-piece prior art structures comprising a base member and a separate post member. The selection is, of course, based on the sizes and shapes of such available structures which best match the particular geometry of the patient's mouth. These structures are then screwed into the implant members and an appropriately shaped prosthesis is cemented thereto.

Instead of utilizing the straight prosthesis support structures or the two-piece support structures of the prior art, a preferred embodiment of the invention contemplates utilizing a one-piece angled support member identified by reference numeral 60 in FIG. 6. Support member 60 is, in one aspect of the invention, made utilizing an article 40 shown schematically in FIG. 4. Article 40 comprises a shank 42 characterized by threads 44 and an upper surface 46. The threads 44 of shank 42 are of a gauge which corresponds to the threaded bore 24 of implant member 20, thereby permitting shank 42 to be screwed therein.

Shank 42, including threads 44 and upper surface 46, are preferably fabricated from any suitable material, such as thermoplastic resins or the like, which can be inexpensively manufactured and formed in the desired shape. The material so used, however, is preferably readily meltable. For example, in one embodiment the material may melt at temperatures between about 100 and 400 degrees Fahrenheit, yet be sufficiently strong to retain its structural integrity at room temperatures.

In application, the shank 42 is used with the conventional dental stone, having analogs 30 formed therein, all as described in detail above. More particularly, a shank 42 is preferably screwed into each of analogs 30 with the upper surface 46 protruding slightly therefrom.

A dental professional then forms on upper surface 46 of each shank 42 a temporary model of a post represented by reference numeral 50 in FIG. 5. The model 50 is preferably formed of a readily meltable and moldable material such as wax, and includes a proximal end 52 and a distal end 54 defining an obtuse angle 59. As with shank 42, the material from which the model 50 is made preferably melts at temperatures between about 100 and 400 degrees Fahrenheit.

Because the model 50 can be molded by a dental professional onto the upper surface 46 of shank 42, and because shank 42 is screwed into a corresponding analog 30 which, in turn, is formed in a dental stone which precisely duplicates the relevant portion of the patient's mouth—including the space 15 for which a prosthesis is needed—the model 50 can be custom formed for any patient. More particularly, the lengths of the proximal end 52 and distal end 54, as well as the size of obtuse angle 59, can be designed so that a prosthesis and its supporting components will precisely fit in the patient's mouth. This should be contrasted with the prior art, where the dental professional is required to select from among a finite number of prefabricated support structures or alloys.

Referring now to FIGS. 11A–11D, there is shown a fixture 80 used for making support member 60 with the aid of analog 30, shank 42 and model 50. As shown in FIG. 11A, for example, there is a fixture 80, typically made of rubber, which preferably defines a base 82 for holding a wax sprue 86 in substantially upright position. Surrounding base 82 is a cylindrical metal form 84.

As shown in FIG. 11B, shank 42, with model 50 formed thereon in the manner previously described, is placed upside down on wax sprue 86. A dental investment 90, is then made by pouring investment material well known to those skilled in the art, into form 84 as shown in FIG. 11C. The investment 90 thus covers model 50, and shank 42, and wax sprue 86.

After investment 90 has hardened, it is preferably removed from fixture 80. The investment 90 is then preferably placed in an oven where model 50, shank 42, and wax sprue 86 are melted by the application of heat. When the melting is completed, and the melted material removed by any convenient means, a mold 95 of a one-piece support structure is left inside investment 90 as shown in FIG. 11D. Mold 95 thus takes on the shape of shank 42 and model 50 which have previously been melted away, along with an end remnant resulting from wax sprue 86. A metallic material, such as gold or an alloy, is then melted, and applied to mold 95 in any conventional way, such as with a casting machine of the type well-known in the art. When the metallic material resolidifies, the investment 90 is broken away or removed, leaving a one-piece angled support member 60 of uniform metallic material as shown in FIG. 6. The end remnant resulting from wax sprue 86 is, of course, removed such as by filing.

Referring again to FIG. 6, support member 60 thus comprises a shank portion 62 having threads 63, and post portion 65 having a proximal portion 66 integrally formed with shank portion 62. Post portion 65 of support member 60 further includes a distal portion 68, defining an obtuse angle 69 with proximal portion 66. Thus, the distal portion 68 of post portion 65 extends at an obtuse angle relative to shank portion 62.

It should now be clear that the one-piece angle support member 60 can be threadedly fastened into the implant members 20 that were previously surgically placed in the patient's mouth. When so fastened, as shown in FIG. 9, each support member 60 extends at the proper orientation, for the proper distance, to permit a prosthesis, such as a crown or bridge, to be precisely fabricated and fit into the mouth. FIG. 10 illustrates such a prosthesis identified by reference numeral 70, attached to support members 60 by any conventional means, such as cement.

In another aspect of the invention, it is unnecessary to separately fabricate the shank 42 shown in FIG. 4. Thus, instead of screwing shank 42 into the analog 30, the threaded bore of analog 30 can be filled with wax or some similar material. The model 50 can then be formed directly onto the top of the wax-filled bore, and the entire wax structure, including the wax in the bore of analog 30, may then be carefully unscrewed and placed in a fixture 80 of the type shown in FIG. 11A. The steps explained in connection with the description of FIGS. 11A-11D may then be repeated.

Similarly, the same results may be obtained by utilizing materials other than wax and/or thermoplastic resins in fabricating model 50 and/or shank 42. For example, model 50 and/or shank 42 may be fabricated from some material which can be disintegrated or decomposed, rather than melted away, after being placed in the fixture 80 shown in FIGS. 11A-11D. Thus, as used herein, the terms "melt" and "meltable," contemplate not only a change of state, but a reaction of the type suggested by such disintegration or decomposition referred to above.

Though the exemplary embodiments disclosed and described herein are preferred, numerous changes and modifications which do not part from the true scope of the invention will be apparent to those skilled in the art. All such changes and modifications are intended to be covered by the appended claims.

We claim:

1. A method of making an article used in the manufacture of a dental prosthesis of the type utilizing an implant member, having a threaded bore, adapted to be placed beneath gum tissue and into underlying bone structure, comprising the following steps:
   providing an analog of said implant member;
   providing a temporary threaded shank, formed of meltable material;
   screwing said shank into said analog; and
   forming on an upper surface of said shank a temporary model of a post for said prosthesis, said model being formed of meltable material.

2. A method of making an article used in the manufacture of a dental prosthesis of the type utilizing an implant member, having a threaded bore, adapted to be placed beneath gum tissue and into underlying bone structure, comprising the following steps:
   providing an analog of said implant member;
   filling the bore of said analog with meltable material forming a shank; and
   forming on an upper surface of said shank a temporary model of a post for said prosthesis, said model being formed of meltable material.

3. The method defined in claims 1 or 2 further including the steps of:
   forming an investment around said model and at least a portion of said shank.

4. The method defined in claim 3 further including the step of:
   melting away said model and said shank to form a mold within said investment for a prosthesis support that can be screwed into the bore of said implant member.

5. The method recited in claim 4 further including the step of: filling said mold with molten material.

6. The method recited in claim 5 further including the step of: allowing said molten material to harden into a one-piece support member of uniform metallic material.

7. The method defined in claim 6 further including the step of: removing said support member from said investment.

8. The method defined in claim 7 further including the step of: screwing said support member into said implant member.

9. The method defined in claim 4, wherein said shank is removed from said analog before said investment is formed therearound.

10. The method defined in claim 4, wherein said melting is accomplished by the application of heat at temperatures of between 100 and 400 degrees Fahrenheit.

11. The method defined in claim 1 or 2, wherein said analog is in dental stone.

12. A method for making a one-piece support member of uniform material used in a dental prosthesis of the type wherein the support member is screwed into the threaded bore of an implant member adapted to be placed beneath gum tissue and into underlying bone structure, comprising the following steps:
   providing an analog of the implant member;
   providing a temporary threaded shank;
   screwing said shank into said analog;
   forming on an upper surface of said shank a temporary model of a post;
   forming an investment about said model and at least a portion of said shank;
   removing said model and said shank from said investment to form a mold of said support member; and
   filling said mold with molten material to form a one-piece support member of uniform material.

13. The method defined in claim 12, further including the step of screwing said support member into the bore of said implant member.

14. The method defined in claim 12, wherein said support member is made of metallic material.

15. The method defined in claim 12, wherein said analog is in dental stone.

16. The method defined in claim 15, wherein said melting is accomplished by the application of heat at temperatures of between about 100 and 400 degrees Fahrenheit.

17. The method defined in claim 12, wherein said model and said shank are removed from said investment by melting said model and said shank.

* * * * *